United States Patent [19]

Birr

[11] Patent Number: 4,485,253

[45] Date of Patent: Nov. 27, 1984

[54] PROCESS FOR PREPARING TERT-BUTYL ETHER OR ESTER CONTAINING POLYFUNCTIONAL ORGANIC COMPOUNDS

[75] Inventor: Christian Birr, Eichendorffstrasse 31, D-6906 Leimen, St. Ilgen, Fed. Rep. of Germany

[73] Assignee: Christian Birr, St. Ilgen, Fed. Rep. of Germany

[21] Appl. No.: 381,989

[22] Filed: May 25, 1982

[30] Foreign Application Priority Data

Jun. 5, 1981 [DE] Fed. Rep. of Germany ....... 3122450

[51] Int. Cl.$^3$ ............................................ C07C 149/40
[52] U.S. Cl. ........................................ 560/9; 560/38; 560/39; 560/170; 560/171
[58] Field of Search ................... 560/247, 9, 169, 170, 560/274, 171, 38, 39

[56] References Cited

U.S. PATENT DOCUMENTS

| | | | |
|---|---|---|---|
| 3,746,689 | 7/1973 | Narayan | 560/171 |
| 4,068,086 | 1/1978 | Dalibor | 560/169 |
| 4,332,965 | 6/1982 | Dalibor | 560/169 |

FOREIGN PATENT DOCUMENTS

| | | | |
|---|---|---|---|
| 656869 | 1/1963 | Canada | 560/247 |
| 2019175 | 10/1970 | Fed. Rep. of Germany | 560/247 |
| 2021825 | 12/1971 | Fed. Rep. of Germany | 560/247 |
| 2158562 | 7/1972 | Fed. Rep. of Germany | 560/171 |
| 382858 | 12/1959 | Japan | 560/247 |
| 936400 | 9/1963 | United Kingdom | 560/247 |

OTHER PUBLICATIONS

Greenstein et al., "Chemistry of Amino Acids" vol. 2, pp. 925–929, Wiley and Sons, Inc. NY, (1961).

Primary Examiner—Werren B. Lone
Attorney, Agent, or Firm—Felfe & Lynch

[57] ABSTRACT

For the preparation of polyfunctional organic compounds having at least one functional group of medium nucleophilic character selectively blocked by a tertiary butyl group, the corresponding unblocked compound is dissolved in a solution of concentrated sulfuric acid in an organic ether, and excess liquid isobutene is added to the solution at a temperature of not more than 5° C.

7 Claims, No Drawings

PROCESS FOR PREPARING TERT-BUTYL ETHER OR ESTER CONTAINING POLYFUNCTIONAL ORGANIC COMPOUNDS

This invention relates to a process for preparing polyfunctional organic compounds having at least one tert-butyl ether or tert-butyl ester group, more specifically compounds having at least one functional group of medium nucleophilic character selectively blocked by a tertiary butyl group.

Organic compounds which contain a plurality of reactive groups of which only one is to be selectively reacted in a subsequent chemical reaction require a selective blocking of the functions which are not to react. Examples of classes of substances in which this is often the case are nucleic acids derivatized on the purine or pyrimidine structure, acid-substituted sugar and amino sugar derivatives, hydroxydicarboxylic acids, aminodicarboxylic acids, hydroxyamino acids and polyacid and/or polybasically substituted derivatives of dicarboxylic acids and amino acids.

Numerous protective groups are already known which are suitable for the blocking of various functional groups. One important property that is required of such protective groups is that they be able to be split off under mild conditions having the least possible effect on the other protective groups or reactive groups.

The protective groups which satisfy this condition include the tertiary butyl group, often referred to as the tBu or $Bu^t$ group. It is suitable, for example, for masking hydroxyl and carboxyl groups. The advantage of their selective cleavability under mild conditions, however, is offset by the disadvantage of a very complex, multistep process for selective introduction, with low yields. This process is described, for example, in Houben-Weyl, *Methoden der organischen Chemie*, Vol. 15/1, p. 579-584 and 649 to 656, Georg Thieme Verlag, Stuttgart 1974. The difficulty of preparing compounds bearing this protective group constitutes a severe handicap to their widespread use.

THE INVENTION

It is therefore the object of the invention to eliminate this disadvantage and to create a simple method permitting the rapid preparation in a high yield, without requiring complex or expensive apparatus, of polyfunctional compounds having at least one function selectively blocked by a tert-butylether group.

This object is achieved in accordance with the invention by a method which is characterized in that a corresponding compound having at least one free group of medium nucleophilia is dissolved in a solution of concentrated acid, e.g. sulfuric acid, in an organic ether, and the solution thus obtained is treated with excess liquid iosbutene at a temperature of no more than $+5°$ C.

The common functional groups occurring in organic compounds have a nucleophilia diminishing in the following order:

$H_2N-$ aliph. $> HS-$ aliph. $> H_2N-$ arom. $> HO-$ aliph. $> HS-$ arom. $> HO-$ arom. $> -COOH$ aliph$(\gamma > \beta > \alpha)$ $-COOH$ arom. $> -OPO_3H_2 > -SO_3H$.

Groups of medium nucleophilia in the above series, again in order of diminishing nucleophilia, are the following:

$HO-$ aliph. $> HS-$ arom. $> HO-$ arom. $> -COOH$ aliph.$(\gamma > \beta > \alpha) > -COOH$ arom.

The groups of this series are selectively blocked in the method of the invention, and as a rule the group that is on the left in this series reacts almost entirely away, before a group further to the right in the series begins to react to an appreciable extent. For example, $HO-$ aliph. reacts in about 30 minutes, and $-COOH$ arom. in about 3 hours. Under the conditions of the process of the invention, the functional groups of highest nucleophilia are blocked by the protons of the sulfuric acid in the solvent mixture. At the same time, the compositions that are to be reacted are dissolved in the solvent. When the dissolution takes place, the compounds that are to be reacted contain only functions of medium and lower nucleophilia. If, then, in accordance with the invention, excess liquefied isobutene is added in the stated temperature range, the groups of very low nucleophilia, such as phosphoric acid monoesters and sulfonic acid groups, no longer react with the isobutene.

Therefore, those polyfunctional organic compounds can be used in the process of the invention which have at least one hydroxyl group, carboxyl group or aromatic sulfhydryl group in addition to other groups of higher or lower nucleophilia. Examples of such compounds are the classes of substances previously mentioned above.

The organic ether used as solvent is selected such that, in the presence of sulfuric acid, the polyfunctional organic compound on which the blocking is to be performed will dissolve therein. Examples of suitable ethers are those derived from polyols with relatively short organic chains, including those with a maximum of 5 carbon atoms. Examples of suitable compounds are the ethers of glycols and polyethylene glycols, such as diethylene glycol dimethyl ether, ethers of polyols of 3 to 5 hydroxyl groups such as glycerol trimethyl ether, higher methoxyalkanes, cyclic ethers such as dioxane and tetrahydrofuran, and dimethoxyethane and the like. Dimethoxyethane is preferred.

To the solution of concentrated acid, e.g. sulfuric acid and the polyfunctional organic compound in the selected ether, excess liquid isobutene is added at temperatures up to a maximum of $+5°$ C., preferably of approximately $0°$ C., and this temperature is sustained, preferably with stirring, until the functional group that is to be blocked has reacted to such an extent that another group of lower nucleophilia begins to be blocked. Normally, the reaction of a group in this case is not quantitative, but is continued only up to a certain equilibrium at which the reaction is mostly completed. At this time the reaction mixture as a rule still contains some of the starting material and usually also smaller amounts of additional reaction products. These, however, can be separated in a very simple manner, as described further below.

As soon as the reaction has progressed to a sufficient extent, the reaction is stopped by rapid removal of the excess remaining isobutene and neutralization of the sulfuric acid. The neutralization is best performed by the addition of a suitable base, for example an alkali hydroxide such as sodium hydroxide. However, other compounds of a sufficiently alkaline reaction can also be used. The excess isobutene can easily be removed by evaporation.

The evaporation is performed to special advantage by vaporization on a large surface. After the separation of any insoluble salts that made have formed in the neutralization of the sulfuric acid, such as sodium sulfate in the case of neutralization with caustic soda solution, the further processing and purification is best performed by extraction with water and chromatographic separation of the aqueous phase. Preferably, ether solvents are largely withdrawn, for example by evaporation in vacuo. The concentrate is dissolved with water and from this solution the desired substance is obtained by crystallization, or the aqueous solution is chromatographed. Molecular sieve and silica materials are especially suitable for the chromatography, also such as cross-linked dextrans, an example being the kind sold under the name of Sephadex. The compounds of the above-named classes with various reactive groups of different nucleophilia are also soluble in water after partial tert-butylation, and therefore they can easily be separated in this manner. The separation by silica chromatography is preferred.

Other suitable chromatography materials are, for example, cellulose esters and ethers, such as acetylcellulose and similar substances. The elution can be performed with water in each case, the individual components being easily separated and obtained in pure form.

The reaction time of the transposition with isobutene is generally between 10 and 120 minutes, but in the case of the groups of lowest nucleophilia within the definition of medium nucleophilia given above, longer reaction times can also occur. Ten to 30 minutes are also to be expected for the halting of the reaction by neutralization and removal of excess reagent, so that, all in all, an extremely quick, simple and economic process is made possible, which greatly reduces the trouble involved in the older methods. Formerly it was necessary to make use of special protective groups for any function that was not to be protected by a tertiary butyl group, and these had to be cleaved off again in a series of additional steps before the actual tertiary butyl compound could be obtained. Among the reaction conditions of the invention, the isobutene is handled without pressure vessels, which is also an important advantage for the practicability of the process.

EXAMPLES

Example 1

Under anhydrous conditions, 55 ml of concentrated sulfuric acid is dissolved with stirring in one liter of 1,2-dimethoxyethane. 50 g of L-glutamic acid is added and dissolved. The mixture is then cooled by external chilling to 0° to +5° C. and 150 ml of liquefied isobutene is added all at once. After stirring while cooling with ice, the reaction is stopped after 90 minutes by pouring the mixture into a tub. Concentrated caustic soda solution is poured into it in an amount equivalent to the amount of sulfuric acid. After stirring, the precipitated sodium sulfate is separated and the filtrate is concentrated in vacuo. The syrupy concentrate is dissolved in a little water and 4 liters of methanol are added to separate the starting material, precipitating glutamic acid. The glutamic acid is filtered out, the filtrate is concentrated in vacuo, the syrupy concentrate is dissolved in a little water, and the solution is applied to a Sephadex LH 20 column (10 to 15 cm diam., length 1.5 m). The column is eluted with water; first L-glutamic acid-α-tert-butyl ester emerges, followed by L-glutamic acid-γ-tert-butyl ester as the main product. Yield of L-glutamic acid-γ-tert-butyl ester: 64%.

Instead of the chromatographic purification, the L-glutamic acid-γ-tert-butyl ester can be obtained from the above-named syrupy raw product by crystallization from water.

Example 2

L-Aspartic acid-β-tert-butyl ester

The procedure of Example 1 was followed using one liter of 1,2-dimethoxyethane as solvent and 120 ml of concentrated sulfuric acid. 80 g of L-aspartic acid was placed in this solution.

The amount of isobutene was 400 ml, and the reaction time 60 minutes from start to stop. The yield was 55% after isolation of the product by crystallization from water.

Example 3

L-Threonine-tert-butylether

The procedure described in Example 1 was followed, but 56 ml of concentrated sulfuric acid, 42 g of L-threonone and 400 ml of isobutene were used. The reaction time was 30 minutes. Yield: 60%.

Example for Purposes of Comparison

Synthesis of glutamic acid-γ-tert-butyl ester in 7 steps similar to known methods The following is an example of the preparation of the compound of Example 1 according to the state of the art.

1. N-benzyloxycarbonyl-glutamic acid (Z-Glu). 147 g (1 mol) of L-glutamic acid is dissolved in 2N NaOH and adjusted to pH 9.5. 205 g of benzyloxycarbonyl chloride, diluted with an equal volume of dioxane, is added drop by drop, with stirring, at 20° C. The pH of the reaction mixture is kept constant at pH 9.5 with 4N NaOH by means of an autotitrator, until no more consumption of NaOH is indicated (approx. 5 h). To work up the product, the reaction solution is brought to pH 11, shaken thrice with ether to remove excess benzyloxycarbonyl chloride, acidified with 2N HCl to pH 2, saturated with NaCl, and thrice extracted with acetic acid ethyl ester. The organic phase is carefully separated, dried with $Na_2SO_4$ and concentrated in vacuo at 40° C. Yield 238 g (85%) M.P. 113° to 114° C. (from acetic acid ethyl ester). $R_F$ value in a 7:1 mixture of benzene and acetic acid: 0.30.

$C_{13}H_{15}NO_6$ (281.27). Calc.: C, 55.51; H, 5.33; N, 4.98. Found: C, 55.50; H, 5.55; N, 5.38.

2. N-Benzyloxycarbonyl-glutamic acid anhydride. 120.8 g (0.43 mol) of Z-Glu is dissolved in 200 ml of anhydrous tetrahydrofuran, and a solution of 98 g of dicyclohexylcarbodiimide in 200 ml of anhydrous tetrahydrofuran is added at 0° C. After 15 h of standing at −20° C. the precipitated dicyclohexylurea is removed with a suction filter and the solvent is withdrawn in vacuo at 30° C. The remanent oil is sufficiently pure for further processing and is immediately reacted. Yield 115 g (100%).

$C_{13}H_{15}NO_5$ (263.25). Calc.: C, 59.31; H, 4.96; N, 5.32. Found: C, 59.54; H, 5.59; N, 6.12.

3. N-Benzyloxycarbonyl-glutamic acid-α-ethyl ester. 113 g (0.43 mol) of Z-glu anhydride is dissolved in one liter of anhydrous ethanol and refluxed for 15 hours. The α- and γ-monoethyl esters of Z-Glu are thus formed successively in a ratio of 1:2. The reaction solution is concentrated in vacuo, the oily residue dissolved with 250 ml of anhydrous ether, 78 g of distilled dicyclohexylamine is added, and the mixture is let stand for 2 days in the refrigerator. The crystallizate of the α- and γ-ester.dicyclohexyl ammonium salts is removed with a suction filter and the mother liquor is concentrated in vacuo to recover Z-glu and saponified for 5 hours with 2N NaOH in dioxane at pH 10.5 on the autotitrator. The dicyclohexylammonium salt mixture is dissolved in 300 ml of ethanol to recover the alpha ester, and approximately 1.5 liters of petrol ether (40° C.) is added until turbidity is produced. It is desirable to add a small amount of previously prepared α-ester.dicyclohexylammonium salt as seed crystals. The α-ester.DCA salt crystallizes uniformly (virtually pure on tlc) at 20° C. in the time period from 0.5 to 4 hours, and is recrystallized two more times from ethanol to which petrol ether (40° C.) is added in a ratio of 1:5 until turbidity occurs. All of the mother liquors are worked up as described above for the recovery of Z-Glu. Yield of Z-Glu-α-ethyl ester.DCA salt 34 g (30%) m.p. 154° C. (from a mixture of ethanol and petrol ether (40° C.). $R_F$ value in a 7:1 mixture of benzene and glacial acetic acid: 0.50.

$C_{27}H_{42}N_2O_6$ (490.65). Calc.: C, 66.25; H, 8.36; N, 5.72. Found: C, 61.47; H, 7.72; N, 5.45.

Z-Glu-γ-ethyl ester DCA salt, M.P. 215° C. (from a mixture of ethanol and petrol ether (40° C.)).

$R_F$ value in a 7:1 mixture of benzene and glacial acetic acid: 0.61.

4. 70 g of the Z-Glu-α-ethyl ester DCA salt is dissolved in 500 ml of acetic acid ethyl ester and thrice extracted with 100 ml of 0.5N $KHSO_4$ solution each time. Then the organic phase is thrice washed with 100 ml of saturated NaCl solution, dried over $Na_2SO_4$ and concentrated in vacuo at 30° C. Yield 48 g (100%); m.p. 46° to 47° C. (recrystallized from a mixture of ethanol and petrol ether (40° C.)); rotation $[\alpha]_D^{19}$ (c=2 in methanol) −22.5° C. for Z-Glu-α-ethyl ester.

$C_{15}H_{19}NO_6$ (309.33). Calc.: C, 58.44; H, 5.84; N, 4.51. Found: C, 58.00; H, 5.84; N, 4.71.

Z-Glu-γ-ethyl ester, m.p. 230° C. (ethanol/petrol ether (40° C.); rotation $[\alpha]_D^{19}$ (c=2 in methanol) −8° C.

5. N-Benzyloxycarbonyl-glutamic acidα-ethyl-γ-tert-butyl ester. 30 g of Z-Glu-α-ethyl ester (0.1 mol) is dissolved in 400 ml of dichlormethane and placed in a glass autoclave. With the exclusion of moisture, 5 ml of concentrated sulfuric acid and approximately 360 ml of liquefied isobutene are added. The mixture is stirred with a magnetic stirrer in the carefully sealed reaction vessel for 4 days at 20° C. Before the vessel is opened, the mixture is chilled down to 0° C. and then transferred to a flask with 200 ml of 5% $Na_2CO_3$ solution. Excess isobutene is aspirated with an air stream into the water jet pump and then the dichlormethane phase is separated. The soda solution is again shaken with dichlormethane, and all of the organic extracts are combined, washed twice with 5% soda solution and thrice with water, dried over $Na_2SO_4$ and concentrated in vacuo at 30° C. The remanent oil is dried in the desiccator over $P_2O_4$. Yield 26 g (90%) of oil.

6. N-Benzyloxycarbonyl-glutamic acid-γ-tert-butyl esterdicyclohexylammonium salt. 36.5 g (0.1 mol) of Z-Glu-(OBu$^t$)OEt is dissolved in 300 ml of dioxane and saponified on the autotitrator at pH 10.5 with 2N NaOH in 5 hours at 20° C. with vigorous stirring. To work up the reaction mixture it is cooled to 0° C., neutralized with 1N HCl and concentrated in vacuo at 40° C. to remove the dioxane. The concentrate is diluted with 100 ml of water, chilled to 0° C., acidified to pH 1.5 with 1N HCl and extracted four times with 100 ml of ether each time. The organic extract is washed once with 50 ml of 5% $NaHCO_3$ solution and saturated NaCl solution, dried over $Na_2SO_4$ and concentrated in vacuo at 30° C. The remanent oil is dissolved with 100 ml of anhydrous ether, 20 g of distilled dicyclohexylamine is added, and the mixture is let stand in the icebox for 12 hours. The separated crystals are filtered out, washed with a little anhydrous, cold ether, and dried. Yield: 48 g (95%); M.P. 133° to 134° C. (from ether); rotation $[\alpha]_D^{19}$ +6° C. (c=2 in methanol). $R_f$ value in a mixture of benzene and glacial acetic acid (7:1) 0.32.

$C_{28}H_{45}N_2O_6$ (505.68). Calc.: C, 66.53; H, 8.91; N, 5.54. Found: C, 67.24; H, 9.31; N, 5.61.

7. L-Glutamicacid-γ-tert-butylester. 43 g (0.85 mol) of Z-Glu(OBu$^t$).DCA is dissolved in 300 ml of ether and shaken twice with 200 ml of 0.5N $KHSO_4$ solution. The ether phase is washed twice with saturated NaCl solution, dried over $Na_2SO_4$ and concentrated in vacuo at 30° C. The concentrate is dissolved in 200 ml of methanol, about 2 g of palladium (10% on active charcoal) is added, and it is hydrogenated in a stream of hydrogen for 7 hours with the aid of a vibrating mixer. A negative $CO_2$ test indicates the end of the splitting off of protective groups. The catalyst is filtered out, rinsed with methanol, and the filtrate is concentrated in vacuo at 30° C. The concentrate is recrystallized from methanol mixed with anhydrous ether. Yield: 19 g (67%); m.p. 184° C. (methanol-ether mixture).

$C_9H_{17}N_1O_4$ (203.25). Calc.: C, 53.20; H, 8.37; N, 6.79. Found: C, 52.52; H, 8.22; N, 6.58.

It will be understood that the specification and examples are illustrative but not limitative of the present invention and that other embodiments within the spirit and scope of the invention will suggest themselves to those skilled in the art.

What is claimed is:

1. Process for preparing amino acids having at least one functional group of medium nucleophilia selectively blocked by a tert.-butyl group, which process comprises dissolving the corresponding unblocked compound in a solution of concentrated sulfuric acid in an organic ether derived from polyols with up to 5 carbon atoms, and adding excess liquid isobutene to the solution at a temperature of not more than 5° C.

2. Process as claimed in claim 1, wherein the sulfuric acid is neutralized as soon as a predominant portion of the functional group to be blocked has reacted with the isobutene.

3. Process as claimed in claim 2, wherein the excess isobutene is removed by evaporation.

4. Process as claimed in claim 3, wherein the evaporation is performed rapidly.

5. Process as claimed in claim 4, wherein the rapid evaporation is effected by vaporization on a large surface.

6. Process as claimed in claim 2, wherein the neutralized mixture is extracted with water and the aqueous phase is chromatographed on a silica material.

7. Process as claimed in claim 2, wherein the neutralized mixture is extracted with water and the product is obtained by crystallization from water.

* * * * *